US009250196B2

(12) United States Patent
Okabe et al.

(10) Patent No.: US 9,250,196 B2
(45) Date of Patent: Feb. 2, 2016

(54) IMAGING DEVICE, SEMICONDUCTOR MANUFACTURING APPARATUS, AND SEMICONDUCTOR MANUFACTURING METHOD

(71) Applicant: Epicrew Corporation, Ohmura-shi (JP)

(72) Inventors: Akira Okabe, Ohnura (JP); Masanori Tanoguchi, Ohmura (JP); Junichi Tomizawa, Ohmura (JP)

(73) Assignee: Epicrew Corporation, Ohmuri-Shi (JP)

( * ) Notice: Subject to any disclaimer, the term of this patent is extended or adjusted under 35 U.S.C. 154(b) by 121 days.

(21) Appl. No.: 13/912,166

(22) Filed: Jun. 6, 2013

(65) Prior Publication Data
US 2014/0220712 A1    Aug. 7, 2014

(30) Foreign Application Priority Data

Feb. 4, 2013  (JP) .................................. 2013-019900

(51) Int. Cl.
  *G06F 19/00*  (2011.01)
  *G01N 21/95*  (2006.01)
  *H01L 21/67*  (2006.01)
  *H01L 21/68*  (2006.01)
(52) U.S. Cl.
  CPC ...... *G01N 21/9501* (2013.01); *H01L 21/67115* (2013.01); *H01L 21/67259* (2013.01); *H01L 21/681* (2013.01); *H01L 2924/0002* (2013.01)
(58) Field of Classification Search
  CPC .............. G06T 7/0004; G01N 23/225; G01N 21/95623; H01L 21/67253; H01L 22/20; H01L 21/67288; C23C 16/52
  USPC .............. 118/712, 713, 8, 16, 166, 168, 715, 118/725; 438/15, 16, 8, 14, 17, 25; 156/345.25; 216/60; 700/31, 245; 427/9, 248.1, 255.23
  See application file for complete search history.

(56) References Cited

U.S. PATENT DOCUMENTS

| 4,479,848 | A  | * | 10/1984 | Otsubo et al. ................... 438/16 |
| 5,274,434 | A  | * | 12/1993 | Morioka et al. ............ 356/237.4 |
| 6,365,423 | B1 | * | 4/2002  | Heinlein ................. H01L 22/24 257/E21.527 |
| 6,924,157 | B1 | * | 8/2005  | Phan et al. ......................... 438/8 |
| 7,201,936 | B2 | * | 4/2007  | Schwarm ................ C23C 16/52 257/E21.525 |
| 8,726,837 | B2 | * | 5/2014  | Patalay et al. .................. 118/713 |
| 2003/0000922 | A1 | * | 1/2003 | Subramanian et al. ......... 216/60 |
| 2005/0121612 | A1 | * | 6/2005 | Okuda et al. ................... 250/311 |
| 2009/0314205 | A1 | * | 12/2009 | Patalay et al. ................. 118/713 |

FOREIGN PATENT DOCUMENTS

| JP | 10-189692   | 7/1998  |
| JP | 10-214876   | 8/1998  |
| JP | 2009130608  | 12/1998 |
| JP | 2005352410  | 6/2007  |
| JP | 2008-227426 | 9/2008  |
| JP | 2009130532  | 7/2010  |
| JP | 2012-094814 | 5/2012  |

* cited by examiner

*Primary Examiner* — McDieunel Marc
(74) *Attorney, Agent, or Firm* — Gard & Kaslow LLP

(57) ABSTRACT

There are provided a susceptor having a recessed wafer mounting section, in which a semiconductor wafer is mounted and which is configured to include a circular bottom portion and a side wall portion, on an upper surface, a reaction chamber in which the susceptor is provided, an imaging unit that is provided above the reaction chamber and images the semiconductor wafer and the wafer mounting section, and an image analysis unit that analyzes the deviation of the semiconductor wafer from the wafer mounting section on the basis of an image captured by the imaging unit.

21 Claims, 4 Drawing Sheets

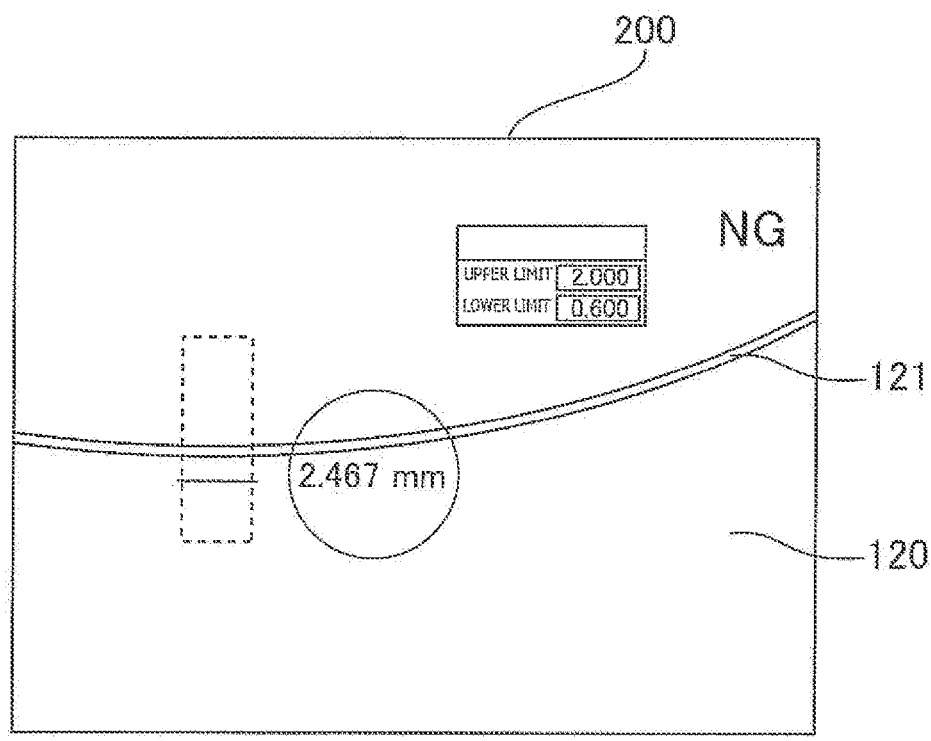
(A)
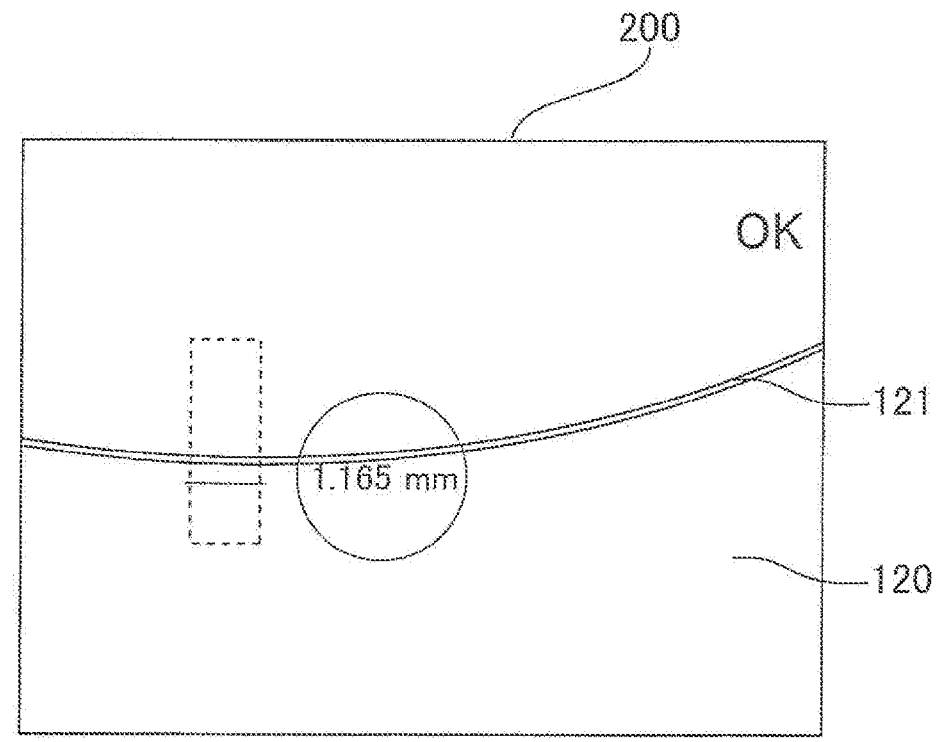
(B)
Fig. 4

IMAGING DEVICE, SEMICONDUCTOR MANUFACTURING APPARATUS, AND SEMICONDUCTOR MANUFACTURING METHOD

BACKGROUND OF THE INVENTION

1. Field of the Invention

The present invention relates to an imaging device, a semiconductor manufacturing apparatus, and a semiconductor manufacturing method and in particular, to an imaging device imaging a semiconductor manufacturing apparatus that grows a crystal layer on a surface of a semiconductor wafer, a semiconductor manufacturing apparatus including the imaging device, and a semiconductor manufacturing method.

2. Background Art

A semiconductor manufacturing apparatus generates a substrate by performing chemical vapor deposition or heat treatment at high temperature on a semiconductor wafer and growing crystals on the surface of a semiconductor wafer. In this case, the semiconductor wafer is generally mounted in a mounting member called a susceptor. The susceptor has a wafer mounting section called a pocket, and the semiconductor wafer is mounted in the wafer mounting section. In addition, by the rotation of the susceptor during deposition, the semiconductor wafer mounted in the susceptor is also rotated. As a result, a uniform crystal layer is formed on the entire wafer surface.

For this reason, it is necessary to pay attention so that the semiconductor wafer is completely seated in the water mounting section during the deposition.

JP-A-2010-199586 discloses a technique of maintaining a semiconductor wafer at a predetermined temperature using a near-infrared emission source and a control system, measuring thermal radiation using a pyrometer, calculating the amplitude of fluctuation of the measurement result of the thermal radiation, estimating that the position of the semiconductor wafer is inappropriate when the amplitude exceeds a predetermined maximum value, and identifying the inappropriate position.

However, the amplitude of fluctuation of the thermal radiation is influenced by the material, of the susceptor or the semiconductor wafer and the like. Therefore, in the method disclosed in JP-A-2010-199586, there is a limit on the accuracy of the deviation that can be detected.

SUMMARY OF THE INVENTION

In view of the above-described situation, it is an object of the invention to provide an imaging device capable of accurately detecting the deviation of a semiconductor wafer from the wafer mounting section, a semiconductor manufacturing apparatus including the imaging device, and a semiconductor manufacturing method.

An imaging device according to an aspect of the invention includes: an imaging unit that images first and second objects placed in a reaction chamber of a semiconductor manufacturing apparatus; and an image analysis unit that analyzes deviation of each of the first and second objects from an appropriate arrangement position on the basis of an image captured by the imaging unit.

The first object may be a semiconductor wafer, and the second object may be a recessed wafer mounting section in which the semiconductor wafer is mounted and which is configured to include a circular bottom portion and a side wall, portion. The deviation may be analyzed by measuring a distance between an end of the semiconductor wafer and the side wall portion of the wafer mounting section on the basis of an image captured by the imaging unit.

The first object may be a susceptor having a recessed wafer mounting section, in which a semiconductor wafer is mounted and which is configured to include a circular bottom portion and a side wall portion, on an upper surface, and the second object may be a preheat ring provided around the susceptor. The deviation may be analyzed by measuring a distance between the susceptor and the preheat ring on the basis of an image captured by the imaging unit.

The susceptor may move up and down, and the imaging unit may image the first and second objects when the susceptor is at a position closest to the imaging unit.

The imaging unit may image a part of the first object and a part of the second object.

The imaging unit may include a light transmissive member that blocks light having a specific wavelength.

The light transmissive member may block infrared rays.

The imaging unit may include an imaging element, a housing case in which the imaging element is housed and the light transmissive member is attached, and coolant supply means for supplying a coolant into the housing case. The light transmissive member may be a quartz glass plate having a gold layer on one or both surfaces.

The housing case may have a gold layer on a surface.

The imaging device may further include a warning notification unit that gives a warning when the deviation exceeds a predetermined value.

The imaging device may further include a display screen for displaying the notification.

The imaging device may further include a setting screen for setting the predetermined value.

The imaging device may further include an image recording unit that records an image captured by the imaging unit.

An imaging device according to another aspect of the invention includes: an imaging unit that images first to fourth objects placed in a reaction chamber of a semiconductor manufacturing apparatus; and an image analysis unit that analyzes deviation of each of the first to fourth objects from an appropriate arrangement position on the basis of an image captured by the imaging unit.

The first object may be a semiconductor wafer, the second object may be a recessed wafer mounting section in which the semiconductor wafer is mounted and which is configured to include a circular bottom portion and a side wall portion, the third object may be a susceptor having the wafer mounting section on an upper surface, and the fourth object may be a preheat ring provided around the susceptor. The deviation may be analyzed by measuring a distance between an end of the semiconductor wafer and the side wall portion of the wafer mounting section and measuring a distance between the susceptor and the preheat ring on the basis of an image captured by the imaging unit.

A semiconductor manufacturing apparatus according to still another aspect of the invention includes: a susceptor having a recessed wafer mounting section, in which a semiconductor wafer is mounted and which is configured to include a circular bottom portion and a side wall portion, on an upper surface; a reaction chamber in which the susceptor is provided; an imaging unit that is provided above the reaction chamber and images first and second objects placed in the reaction chamber; and an image analysis unit that analyzes deviation of each of the first and second objects from an appropriate arrangement position on the basis of an image captured by the imaging unit.

The first object may be the semiconductor wafer, and the second object may be the wafer mounting section. The deviation may be analyzed by measuring a distance between an end of the semiconductor wafer and a side wall portion of the wafer mounting section on the basis of an image captured by the imaging unit.

The first object may be the susceptor, and the second object may be a preheat ring provided around the susceptor. The deviation may be analyzed by measuring a distance between the susceptor and the preheat ring on the basis of an image captured by the imaging unit.

The susceptor may move up and down, and the imaging unit may image the first and second objects when the susceptor is at a position closest to the imaging unit.

The susceptor may have a target that is a focus when the imaging unit images the first, and second objects.

The imaging unit may image a part of the first object and a part of the second object.

The imaging unit may include a light transmissive member that blocks light having a specific wavelength.

The light transmissive member may block infrared rays.

The imaging unit may include an imaging element, a housing case in which the imaging element is housed and the light transmissive member is attached, and coolant supply means for supplying a coolant into the housing case. The light transmissive member may be a quartz glass plate having a gold layer on one or both surfaces.

The housing case may have a gold layer on a surface.

The semiconductor manufacturing apparatus may further include a warning notification unit that gives a warning when the deviation exceeds a predetermined value.

The semiconductor manufacturing apparatus may further include a display screen for displaying the notification.

The semiconductor manufacturing apparatus may further include a setting screen for setting the predetermined value.

The semiconductor manufacturing apparatus may further include an image recording unit that records an image captured by the imaging unit.

The semiconductor manufacturing apparatus may further include a heating unit that is provided above the reaction chamber in order to heat the semiconductor wafer.

The heating unit may be a heat source that emits infrared rays.

A semiconductor manufacturing apparatus according to still another aspect of the invention includes: a susceptor having a recessed wafer mounting section, in which a semiconductor wafer is mounted and which is configured to include a circular bottom portion and a side wall portion, on an upper surface; a reaction chamber in which the susceptor is provided; an imaging unit that is provided above the reaction chamber and images first to fourth objects placed in the reaction chamber; and an image analysis unit that analyzes deviation of each of the first to fourth objects from an appropriate arrangement position on the basis of an image captured by the imaging unit.

The first object may be the semiconductor wafer, the second object may be the recessed wafer mounting section, the third object may be the susceptor, and the fourth object may be a preheat ring provided around the susceptor. The deviation may be analyzed by measuring a distance between an end of the semiconductor wafer and a side wall portion of the wafer mounting section and measuring a distance between the susceptor and the preheat ring on the basis of an image captured by the imaging unit.

A semiconductor manufacturing method according to still another aspect of the invention includes imaging first and second objects placed in a reaction chamber; and analyzing deviation each of the first and second objects from an appropriate arrangement position on the basis of a captured image.

The first object may be a semiconductor wafer, and the second object may be a recessed wafer mounting section in which the semiconductor wafer is mounted and which is configured to include a circular bottom portion and a side wall portion. The deviation is analyzed by measuring a distance between an end of the semiconductor wafer and the side wall portion of the wafer mounting section on the basis of an image captured by the imaging unit.

The first object may be a susceptor having a recessed wafer mounting section, in which a semiconductor wafer is mounted and which is configured to include a circular bottom portion and a side wall portion, on an upper surface, and the second object may be a preheat ring provided around the susceptor. The deviation may be analyzed by measuring a distance between the susceptor and the preheat ring on the basis of an image captured by the imaging unit.

Since the imaging device according to the aspect of the invention includes an imaging unit that images a semiconductor wafer and a recessed wafer mounting section, in which the semiconductor wafer is mounted and which is configured to include a circular bottom portion and a side wall portion, and an image analysis unit that analyzes the deviation of the semiconductor wafer from the wafer mounting section on the basis of an image captured by the imaging unit, it is possible to detect the deviation of the semiconductor wafer from the appropriate mounting position on the wafer mounting section with high accuracy.

Since the wafer mounting section is provided on the susceptor having a preheat ring therearound, the imaging unit images the susceptor and the preheat ring, and the image analysis unit analyzes the distance between the susceptor and the preheat ring on the basis of the image captured by the imaging unit, it is possible to notice the need for maintenance early, for example, when there is a problem in a direction of vertical movement of the susceptor.

In addition, when the imaging unit images a part of the semiconductor wafer and a part of the wafer mounting section, the deviation of the semiconductor wafer from the appropriate position can be imaged in an enlarged manner by limiting the imaging range. Accordingly, fine deviation can also be analyzed.

In addition, since the deviation is analyzed by measuring the distance between the end of the semiconductor wafer and the side wall portion on the basis of an image captured by the imaging unit, it is possible to detect the deviation of the semiconductor wafer from the appropriate mounting position on the wafer mounting section with high accuracy.

In addition, since the imaging unit includes a light transmissive member that blocks light having a specific wavelength, it is possible to prevent the image captured by the imaging unit from being overexposed (dimming) due to too strong light emitted from the heat source (excessive amount of light).

In addition, since the light transmissive member blocks infrared rays, it is possible to prevent the image captured by the imaging unit from being overexposed by infrared rays emitted from the heat source.

In addition, since the imaging unit includes an imaging element, a housing case in which the imaging element is housed and the light transmissive member is attached, and coolant supply means for supplying a coolant into the housing case and the light transmissive member is a quartz glass plate having a gold layer on one or both surfaces, the imaging unit can have a high heat resistance.

In addition, since the housing case has a gold layer on a surface, the housing case can reflect infrared rays. Therefore, it is possible co prevent the inside of the housing case from becoming hot.

The susceptor can move up and down, and the imaging unit images the semiconductor wafer and the wafer mounting section when the susceptor is at the position closest to the imaging unit. Therefore, it is possible to detect the deviation of the semiconductor wafer from the appropriate mounting position on the wafer mounting section with high accuracy.

In addition, since the imaging device further includes a warning notification unit that gives a warning when the distance between the end of the semiconductor wafer and the side wall portion and/or the distance between the susceptor and the preheat ring exceeds a predetermined value, it is possible to immediately notify the deviation of the semiconductor wafer from the appropriate mounting position on the wafer mounting section.

In addition, since the imaging device further includes a display screen for displaying the notification, it is possible to immediately notify the deviation of the semiconductor wafer from the appropriate mounting position on the wafer mounting section.

In addition, since the imaging device further includes a setting screen for setting the predetermined value, it is possible to arbitrarily set the allowable value of the deviation for each user.

In addition, since the imaging device further includes an image recording unit that records an image captured by the imaging unit, the user can check the state of deviation of the semiconductor wafer from the appropriate mounting position on the wafer mounting section later.

Since the semiconductor manufacturing apparatus according so the aspect of the invention includes a susceptor having a recessed wafer mounting section, in which a semiconductor wafer is mounted and which is configured to include a circular bottom portion and a side wall portion, on an upper surface, a reaction chamber in which the susceptor is provided, an imaging unit that is provided above the reaction chamber and images the semiconductor wafer and the wafer mounting section, and an image analysis unit that analyzes deviation of the semiconductor wafer from the wafer mounting section on the basis of an image captured by the imaging unit, it is possible to detect the deviation of the semiconductor wafer from the appropriate mounting position on the wafer mounting section with high accuracy.

In addition, when the imaging unit images a part of the semiconductor wafer and a part of the wafer mounting section, the deviation of the semiconductor wafer from the appropriate position can be imaged in an enlarged manner by limiting the imaging range. Accordingly, fine deviation can also be analyzed.

In addition, since the deviation is analyzed by measuring the distance between the end of the semiconductor wafer and the side wall portion on the basis of an image captured by the imaging unit, it is possible to detect the deviation of the semiconductor wafer from the appropriate mounting position on the wafer mounting section with high accuracy.

In addition, since the semiconductor manufacturing apparatus further includes a preheat ring around the susceptor, the imaging unit images the susceptor and the preheat ring, and the image analysis unit analyzes the distance between the susceptor and the preheat ring on the basis of the image captured by the imaging unit, it is possible to notice the need for maintenance early, for example, when there is a problem in a direction of vertical movement, of the susceptor.

In addition, since the semiconductor manufacturing apparatus further includes a heating unit that is provided above the reaction chamber in order to heat the semiconductor wafer, it is possible to keep the reaction chamber in the high temperature atmosphere.

Since the heating unit is a heat source that emits infrared rays, it is possible to keep the reaction chamber in the high temperature atmosphere.

Since the imaging unit includes a light transmissive member that blocks light having a specific wavelength, it is possible to prevent the image captured by the imaging unit from being overexposed due to too strong light emitted from the heat source.

Since the light transmissive member blocks infrared rays, it is possible to prevent the image captured by the imaging unit from being overexposed by infrared rays emitted from the heat source.

In addition, since the imaging unit includes an imaging element, a housing case in which the imaging element is housed and the light transmissive member is attached, and coolant supply means for supplying a coolant into the housing case and the light transmissive member is a quartz glass plate having a gold layer on one or both surfaces, the imaging unit can have a high heat resistance.

In addition, since the housing case has a gold layer on a surface, the housing case can reflect infrared rays. Therefore, it is possible to prevent the inside of the housing case from becoming hot.

In addition, the susceptor can move up and down within the reaction chamber, and the imaging unit images the semiconductor wafer and the wafer mounting section when the susceptor is at the position closest to the imaging unit. Therefore, it is possible to detect the deviation of the semiconductor wafer from the appropriate mounting position on the wafer mounting section with high accuracy.

In addition, since the susceptor has a target that is a focus when the imaging unit images the semiconductor wafer and the wafer mounting section, it is possible to adjust the focus of the imaging unit in a state where the imaging unit is provided in the semiconductor manufacturing apparatus.

In addition, since the semiconductor manufacturing apparatus further includes a warning notification unit that gives a warning when the distance between the end of the semiconductor wafer and the side wall portion and/or the distance between the susceptor and the preheat ring exceeds a predetermined value, it is possible to immediately notify the deviation of the semiconductor wafer from the appropriate mounting position on the wafer mounting section.

In addition, since the semiconductor manufacturing apparatus further includes a display screen for displaying the notification, it is possible to immediately notify the deviation of the semiconductor wafer from the appropriate mounting position on the wafer mounting section.

In addition, since the semiconductor manufacturing apparatus further includes a setting screen for setting the predetermined value, it is possible to arbitrarily set the allowable value of the deviation for each user.

In addition, since the semiconductor manufacturing apparatus further includes an image recording unit that records an image captured by the imaging unit, the user can check the state of deviation of the semiconductor wafer from the appropriate mounting position on the wafer mounting section later.

BRIEF DESCRIPTION OF THE DRAWINGS

FIGS. 4A and 4B are schematic diagrams showing a warning notification screen in the embodiment of the invention.

DETAILED DESCRIPTION OF THE INVENTION

Hereinafter, an embodiment of the invention will be described with reference to FIGS. 1 to 4.

Figure 1:
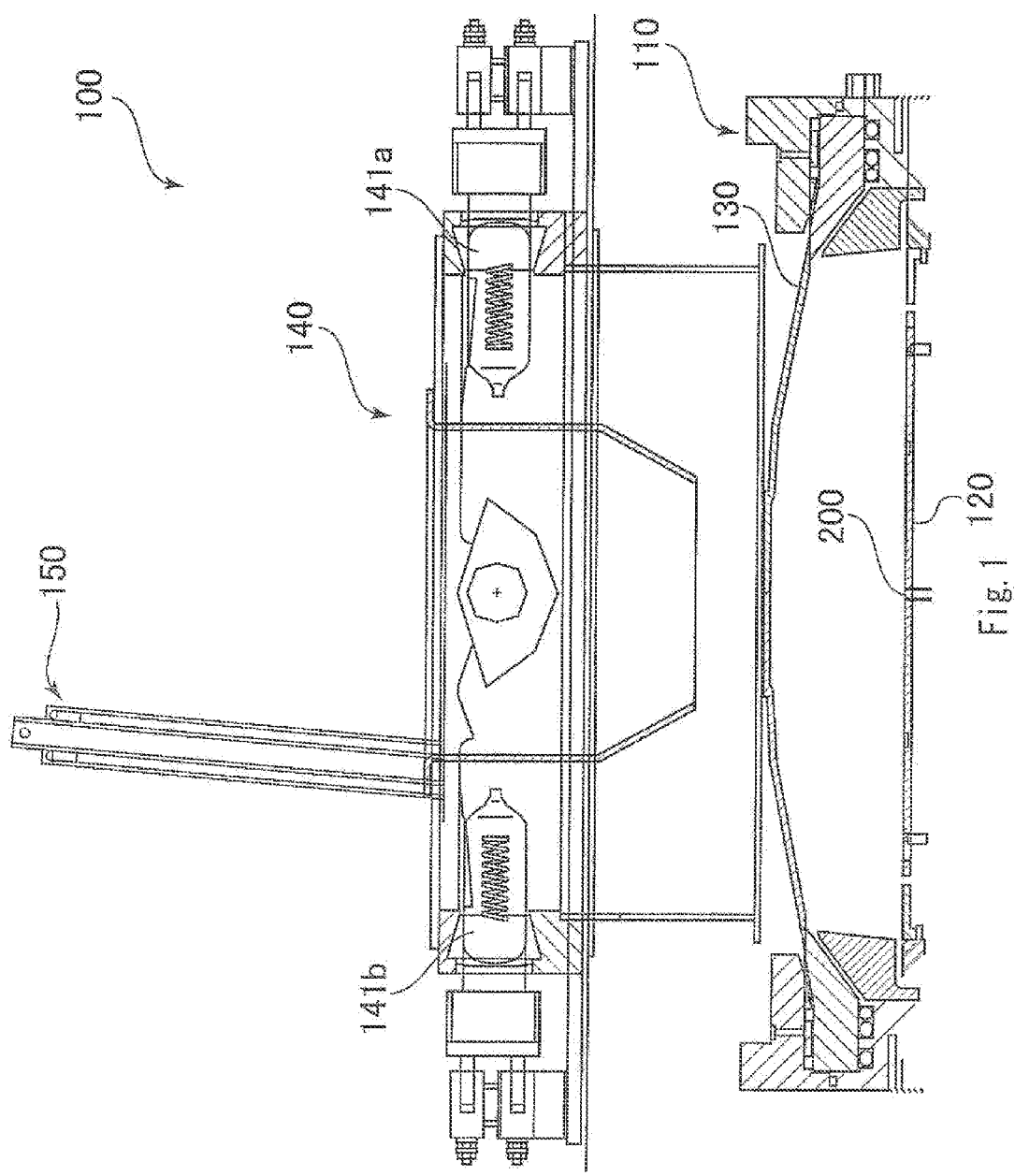
FIG. 1 is a schematic diagram of a semiconductor manufacturing apparatus including an imaging device in an embodiment of the invention.

FIG. 1 is a schematic diagram of a semiconductor manufacturing apparatus 100 including an imaging device (imaging unit 150) according to the present embodiment.

The semiconductor manufacturing apparatus 100 according to the present embodiment performs processing for forming an epitaxial layer as a crystal layer on the surface of a semiconductor wafer 200.

As shown in FIG. 1, the semiconductor manufacturing apparatus 100 includes a susceptor 120, a reaction chamber 110, an imaging unit 150 as an imaging device, and an image analysis unit (not shown). By providing the imaging unit 150 and the image analysis unit, the semiconductor manufacturing apparatus 100 has a function capable of detecting deviation when the deviation occurs in the mounting position of the semiconductor wafer 200.

Each configuration will be described.

The reaction chamber 110 can be sealed, and reactive gas is filled therein. Therefore, by changing the atmosphere of the reaction chamber 110 to a high temperature atmosphere, it is possible no grow an epitaxial layer on the surface of the semiconductor wafer 200. In the reaction chamber 110, the susceptor 120 for mounting the semiconductor wafer 200 is provided.

A lamp unit 140 as a heating unit for heating a semiconductor wafer is provided above the reaction chamber 110. The lamp unit 140 is formed by halogen lamps 141a and 141b. Since the halogen lamps 141a and 141b are heat sources that emit infrared rays, it is possible to make a high temperature atmosphere by illuminating the reaction chamber 110. In addition, the top of the reaction chamber 110 is covered with a quartz dome 130.

Figure 2:
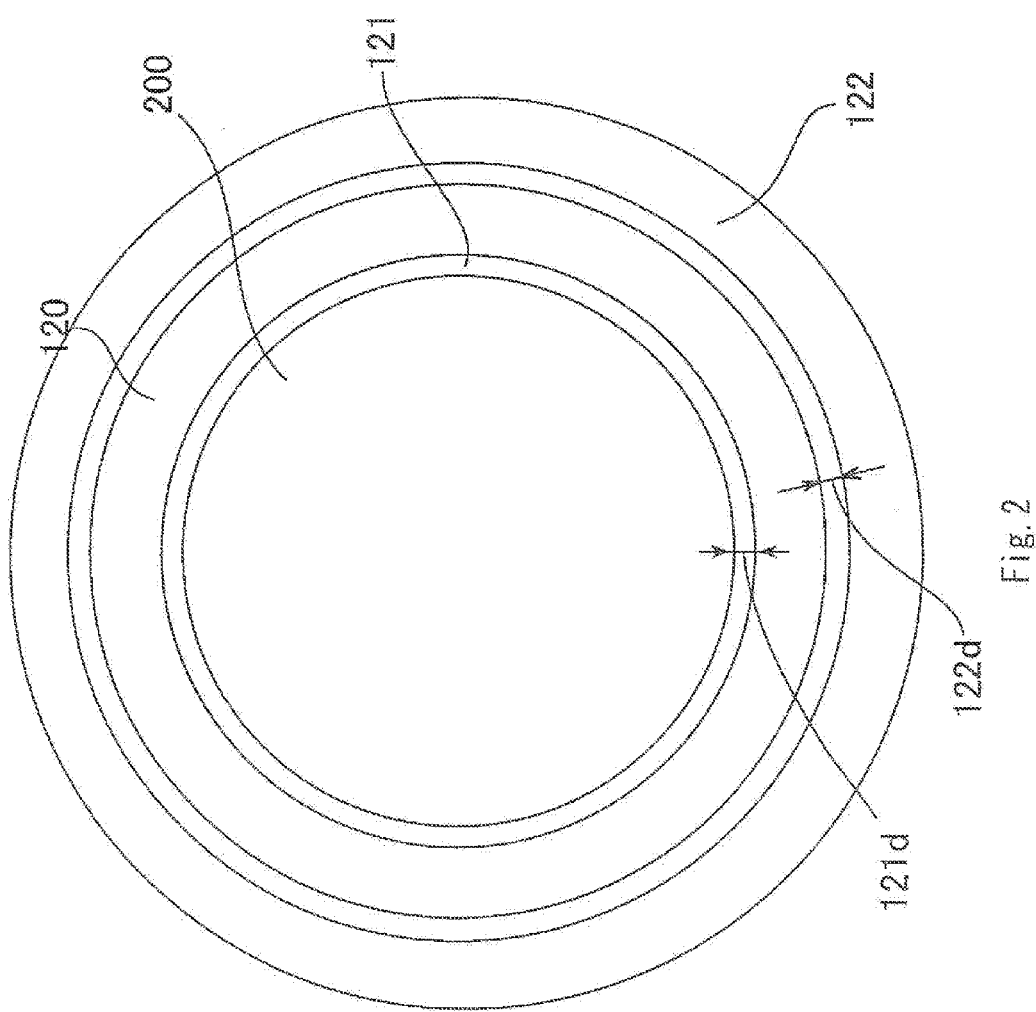
FIG. 2 is a diagram showing the surface of a susceptor in the embodiment of the invention.
Figure 3:
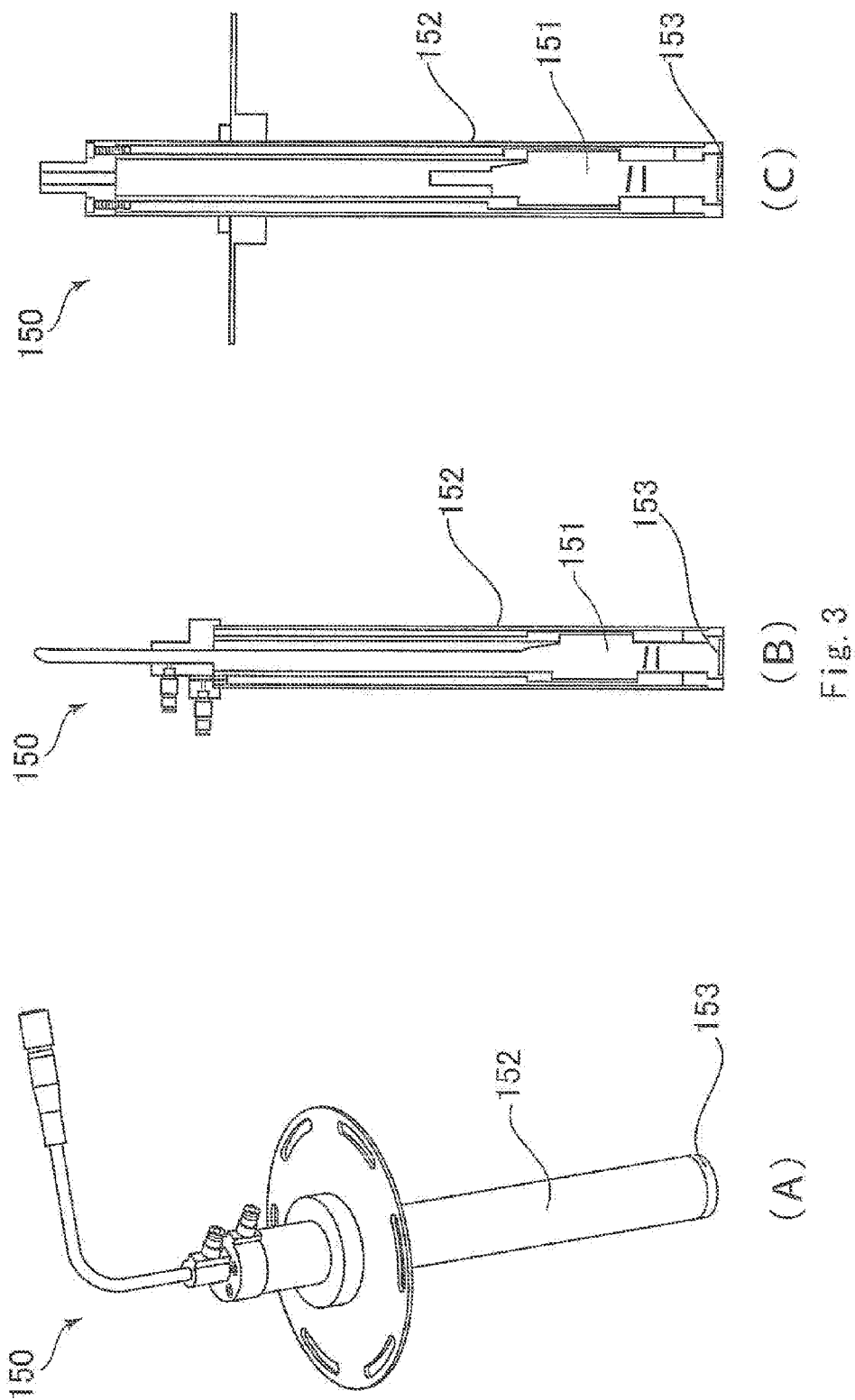
FIGS. 3A to 3C are diagrams showing the outline of an imaging unit in the embodiment of the invention.

The susceptor a member for mounting the semiconductor wafer 200. FIG. 2 is a plan view of the susceptor 120.

As shown in FIG. 2, a recessed wafer mounting section 121 including a circular bottom portion and a side wall portion is provided in the middle of the susceptor 120. The semiconductor wafer 200 is mounted in the wafer mounting section 121.

Preferably, the susceptor 120 moves upward within the reaction chamber 110 when the semiconductor wafer 200 is mounted, and rotates around the central axis when the susceptor 120 has moved to the upper end of the movable range. This is because an epitaxial layer can be uniformly grown on the surface of the semiconductor wafer 200 by the rotation of the susceptor 120. For this reason, it preferable that the semiconductor wafer 200 be mounted in the middle of the wafer mounting section 121. Specifically, a gap 121d between the edge of the semiconductor wafer 200 and the side wall portion of the wafer mounting section 121 needs so be a fixed distance from any point of the edge of the semiconductor wafer. This is because there is a possibility that the epitaxial layer formed on the surface will be uneven when the semiconductor wafer is mounted on the position deviated from the center.

In addition, a preheat ring 122 for warming reactive gas filled in the reaction chamber 110 in advance is provided around the susceptor 120.

As shown in FIG. 1, the imaging unit 150 is provided above the lamp unit 140. An image captured by the imaging unit 150 is transmitted to the image analysis unit to be described later.

The imaging unit 150 images a part of the semiconductor wafer 200 and a part of the wafer mounting section 121 in order to detect the occurrence of the deviation that causes unevenness. More specifically, the imaging unit 150 images the gap 121d between the end of the semiconductor wafer 200 and the side wall portion of the wafer mounting section 121. In addition, it is preferable that the imaging unit 150 image the susceptor 120 and the preheat ring 122. In this case, the semiconductor manufacturing apparatus 100 can analyze not only the gap 121d between the semiconductor wafer 200 and the wafer mounting section 121 but also a gap 122d between the susceptor 120 and the preheat ring 122.

Next, the internal structure of the imaging unit 150 will be described in detail with reference to FIGS. 31 to 3C.

FIGS. 3A to 3C are schematic diagrams of the imaging unit 150. FIG. 3A shows the outer appearance, and FIGS. 3B and 3C show the cross-sectional structure.

As shown in FIG. 31, the imaging unit 150 has a housing case 152. In addition, as shown in FIGS. 3B and 3C, a CCD camera 151 is provided inside the imaging unit 150.

As shown in FIGS. 3A to 3C, it is preferable that the imaging unit. 150 include a light transmissive member 153 at the distal end of the housing case 152. In the reaction chamber 110, intense infrared rays are generated by illumination using the halogen lamps 141a and 141b. Therefore, for example, when observing the reaction chamber 110 with the naked eye, the internal state cannot be observed since the field of view is cloudy. The light transmissive member 153 blocks some of light beams emitted from the reaction chamber 110 in order to prevent the image captured by the CCD camera 151 from being overexposed.

It is preferable that the light transmissive member 153 be a quartz glass plate having a gold layer on its one or both surfaces. Since this prevents heat rays emitted from the halogen lamps 141a and 141b from reaching the CCD camera 151, it is possible to improve the heat resistance of the CCD camera 151.

In addition, it is preferable that the housing case 152 have a gold layer on its surface. This is because infrared rays can be reflected by the gold layer and accordingly it is prevented that the internal temperature of the housing case 152 becomes high.

In addition, it is preferable that the imaging unit 150 have coolant supply means for supplying nitrogen for cooling or the like into the housing case 152. This is because the air around the reaction chamber 110 is heated due to the high temperature atmosphere of the reaction chamber 110 and accordingly it is necessary to suppress an increase in the temperature around the CCD camera 151.

In the imaging unit 150, in order to capture an image with high accuracy, it is necessary to adjust the focal length. For example, if the susceptor 120 has a target, such as a scale, on the surface, it is possible to adjust the focal length in a state where the imaging unit 150 is provided in the semiconductor manufacturing apparatus 100.

In addition, if the semiconductor manufacturing apparatus 100 is configured to include an image recording unit (not shown) chat records an image captured by the imaging unit. 150, it is possible to check which semiconductor wafer 200 has poor quality later even if a user takes his or her eyes off during deposition processing on the semiconductor wafer 200. This image recording unit records an image when a distance of the gap 121d between the semiconductor wafer 200 and the wafer mounting section 121 exceeds a range of a predetermined value and discards an image corresponding to a normal value, so that it is possible to use a hard disk resource effectively.

The image analysis unit extracts a still image from the image captured by the imaging unit 150, and analyzes the distance of the gap 121d. Thus, since the semiconductor manufacturing apparatus 100 includes the susceptor 120 having the wafer mounting section 121, the imaging unit. 150, and the image analysis unit, it is possible to detect the deviation of the semiconductor wafer 200 from the appropriate mounting position with high accuracy. In order to obtain the analysis result with higher accuracy, it is preferable that the image analysis unit extract an image, which is captured when the susceptor 120 is at the position closest to the imaging unit 150, as a still image.

In addition, when the imaging unit 150 images the susceptor 120 and the preheat ring 122 further, the image analysis unit can analyze the distance of the gap 122d between the edge of the susceptor 120 and the edge of the preheat ring 122. Therefore, for example, when there is a problem in a direction of vertical movement of the susceptor 120, it is possible to notice the need for maintenance early.

In addition, it is preferable that the semiconductor manufacturing apparatus 100 have a warning notification unit (not shown) so that the analysis result of the image analysis unit can be fed back to the user. This feedback may be a notification to the user using sound, or may be a display screen to be described later.

FIGS. 4A and 4B are diagrams showing an example of a display screen that displays a notification from the warning notification unit. In this example, when the gap 121d is not in the range of 0.600 mm to 2.000 mm, the warning notification unit gives a warning. It is preferable that the warning notification unit display the word OK on the screen when the analysis result is in a range of a predetermined value (FIG. 4B) and display the word NG on the screen when the analysis result is out of the range of the predetermined value (FIG. 4A). In this case, when the semiconductor wafer 200 deviates from the appropriate mounting position, it is possible to notice the deviation while the semiconductor wafer 200 is in the reaction chamber 110. As a result, it is possible to save the time and effort to check the quality after forming an epitaxial layer.

In addition, it is preferable that the user can freely set a predetermined value for notifying the warning from the setting screen. In the semiconductor manufacturing apparatus 100 of the present embodiment, warning display and value setting can be performed on the same screen. For example, the user can set a predetermined value from the window displayed in FIG. 4A.

While the embodiment of the invention has been described, the invention is not limited to the embodiment described above, and various modifications and changes may be made based on the technical scope of the invention.

For example, although the semiconductor manufacturing apparatus 100 that forms an epitaxial layer using reactive gas has been described in the above embodiment, other semiconductor manufacturing apparatuses may also be used.

In addition, in the explanation of the above embodiment, the warning notification unit displays NG on the warning notification screen when the deviation occurs. However, the invention is not limited to this. For example, it is also possible to give a warning to an external device that mounts a semiconductor wafer on the susceptor and to correct the mounting position.

In addition, the image recording unit may be configured to record an image captured by the imaging unit 150 so as to match the lot number of the semiconductor wafer. In this case, the user can immediately see whether or not there has been deviation in the semiconductor wafer when checking an image later.

What is claimed is:

1. An imaging device comprising:
an imaging unit that images first and second objects placed in a reaction chamber of a semiconductor manufacturing apparatus; and
an image analysis unit that analyzes deviation of each of the first and second objects from an appropriate arrangement position by measuring a distance between the first object and the second object on the basis of an image captured by the imaging unit;
an image recording unit that records both the image captured by the imaging unit and a lot number of a semiconductor wafer;
a display screen for displaying states of the first and second objects;
a warning notification unit that gives a warning on the display screen when the deviation exceeds a predetermined value; and
a setting screen for setting the predetermined value.

2. The imaging device according to claim 1,
wherein the first object is the semiconductor wafer,
the second object is a recessed wafer mounting section in which the semiconductor wafer is mounted and which is configured to include a circular bottom portion and a side wall portion, and
the deviation is analyzed by measuring a distance between an end of the semiconductor wafer and the side wall portion of the wafer mounting section on the basis of an image captured by the imaging unit.

3. The imaging device according to claim 1,
wherein the first object is a susceptor having a recessed wafer mounting section, in which the semiconductor wafer is mounted and which is configured to include a circular bottom portion and a side wall portion, on an upper surface,
the second object is a preheat ring provided around the susceptor, and
the deviation is analyzed by measuring a distance between the susceptor and the preheat ring on the basis of an image captured by the imaging unit.

4. The imaging device according to claim 3,
wherein the susceptor is movable up and down, and
the imaging unit images the first and second objects when the susceptor is at a position closest to the imaging unit.

5. The imaging device according to claim 1,
wherein the imaging unit images a part of the first object and a part of the second object.

6. The imaging device according to claim 1,
wherein the imaging unit includes a light transmissive member that blocks light having a specific wavelength.

7. The imaging device according to claim 6,
wherein the light transmissive member blocks infrared rays.

8. The imaging device according to claim 6,
wherein the imaging unit includes an imaging element, a housing case in which the imaging element is housed and the light transmissive member is attached, and coolant supply means for supplying a coolant into the housing case, and
the light transmissive member is a quartz glass plate having a gold layer on one or both surfaces.

9. The imaging device according to claim 8,
wherein the housing case has a gold layer on a surface.

10. A semiconductor manufacturing apparatus comprising:
a susceptor having a recessed wafer mounting section, in which a semiconductor wafer is to be mounted and which is configured to include a circular bottom portion and a side wall portion, on an upper surface;
a reaction chamber in which the susceptor is provided;
an imaging unit that is provided above the reaction chamber and images first and second objects placed in the reaction chamber; and
an image analysis unit that analyzes deviation of each of the first and second objects from an appropriate arrangement position by measuring a distance between the first and second object on the basis of an image captured by the imaging unit
an image recording unit that records both the image captured by the imaging unit and a lot number of a semiconductor wafer;
a display screen for displaying states of the first and second objects;
a warning notification unit that gives a warning on the display screen when the deviation exceeds a predetermined value; and
a setting screen for setting the predetermined value.

11. The semiconductor manufacturing apparatus according to claim 10,
wherein the first object is the semiconductor wafer,
the second object is the wafer mounting section, and
the deviation is analyzed by measuring a distance between an end of the semiconductor wafer and a side wall portion of the wafer mounting section on the basis of an image captured by the imaging unit.

12. The semiconductor manufacturing apparatus according to claim 10,
wherein the first object is the susceptor,
the second object is a preheat ring provided around the susceptor, and
the deviation is analyzed by measuring a distance between the susceptor and the preheat ring on the basis of an image captured by the imaging unit.

13. The semiconductor manufacturing apparatus according to claim 10,
wherein the susceptor is movable up and down, and
the imaging unit images the first and second objects when the susceptor is at a position closest to the imaging unit.

14. The semiconductor manufacturing apparatus according to claim 10,
wherein the susceptor has a target that is a focus when the imaging unit images the first and second objects.

15. The semiconductor manufacturing apparatus according to claim 10,
wherein the imaging unit images a part of the first object and a part of the second object.

16. The semiconductor manufacturing apparatus according to claim 10,
wherein the imaging unit includes a light transmissive member that blocks light having a specific wavelength.

17. The semiconductor manufacturing apparatus according to claim 16,
wherein the light transmissive member blocks infrared rays.

18. The semiconductor manufacturing apparatus according to claim 16,
wherein the imaging unit includes an imaging element, a housing case in which the imaging element is housed and the light transmissive member is attached, and coolant supply means for supplying a coolant into the housing case, and
the light transmissive member is a quartz glass plate having a gold layer on one or both surfaces.

19. The semiconductor manufacturing apparatus according to claim 18,
wherein the housing case has a gold layer on a surface.

20. The semiconductor manufacturing apparatus according to claim 10, further comprising:
a heating unit that is provided above the reaction chamber in order to heat the semiconductor wafer.

21. The semiconductor manufacturing apparatus according to claim 20,
wherein the heating unit is a heat source that emits infrared rays.

* * * * *